(12) United States Patent
DiMeo, Jr. et al.

(10) Patent No.: US 6,897,960 B2
(45) Date of Patent: May 24, 2005

(54) OPTICAL HYDROGEN DETECTOR

(76) Inventors: Frank DiMeo, Jr., 27 Crows Nest La., Unit 19G, Danbury, CT (US) 06810; Mackenzie E. King, 158 Luther Dr., Southbury, CT (US) 06488

( * ) Notice: Subject to any disclaimer, the term of this patent is extended or adjusted under 35 U.S.C. 154(b) by 0 days.

(21) Appl. No.: 10/138,092

(22) Filed: May 2, 2002

(65) Prior Publication Data

US 2002/0171839 A1 Nov. 21, 2002

Related U.S. Application Data

(63) Continuation-in-part of application No. 09/442,568, filed on Nov. 18, 1999.

(51) Int. Cl.$^7$ .............................................. G01N 21/00
(52) U.S. Cl. ...................... 356/437; 436/144; 436/147; 422/83; 422/88; 73/31.06
(58) Field of Search ................................ 356/432–440; 73/23.2, 31.05–31.06, 24.02, 25.03; 436/164, 144, 147, 167; 422/91, 86; 250/339.01, 339.06, 339.12, 339.13

(56) References Cited

U.S. PATENT DOCUMENTS

| | | |
|---|---|---|
| 3,768,975 A | 10/1973 | Toy |
| 3,951,603 A | 4/1976 | Obayashi et al. |
| 3,953,173 A | 4/1976 | Obayashi et al. |
| 4,058,368 A | 11/1977 | Svensson et al. |
| 4,574,095 A | 3/1986 | Baum et al. |
| 4,661,320 A * | 4/1987 | Ito et al. .......................... 422/86 |
| 4,836,012 A * | 6/1989 | Doty et al. .................. 73/31.06 |
| 4,892,834 A | 1/1990 | Rauh |
| 5,279,795 A | 1/1994 | Hughes et al. |
| 5,287,725 A * | 2/1994 | Zhao et al. .................... 73/23.2 |
| 5,317,897 A * | 6/1994 | Jelley et al. ................. 73/31.06 |
| 5,417,821 A | 5/1995 | Pyke |
| 5,520,753 A | 5/1996 | Hunter |
| 5,635,729 A | 6/1997 | Griessen et al. |
| 5,652,433 A | 7/1997 | Ouwekerk et al. |
| 5,668,301 A * | 9/1997 | Hunter ......................... 73/23.2 |
| 5,670,115 A | 9/1997 | Cheng et al. |
| 5,691,465 A * | 11/1997 | Carr et al. .................. 73/24.02 |
| 5,733,506 A | 3/1998 | Silver et al. |
| 5,783,152 A | 7/1998 | Nave |
| 6,006,582 A * | 12/1999 | Bhandari et al. ............. 73/23.2 |
| 6,185,344 B1 * | 2/2001 | Bevenot et al. ................ 385/12 |
| 6,230,545 B1 * | 5/2001 | Adolph et al. .............. 73/31.05 |
| 6,265,222 B1 * | 7/2001 | DiMeo et al. ............... 436/144 |
| 6,269,680 B1 * | 8/2001 | Prieve et al. ............... 73/23.21 |
| 6,463,789 B2 * | 10/2002 | Moos et al. ................ 73/31.06 |
| 6,535,658 B1 * | 3/2003 | Mendoza et al. ............. 385/12 |
| 6,561,690 B2 * | 5/2003 | Balestriero et al. ......... 362/555 |
| 6,565,239 B2 * | 5/2003 | Rizkin et al. ............... 362/373 |

(Continued)

OTHER PUBLICATIONS

Griessen–R et al., "Yttrium and lanthanum hydride Films with Switchable Optical Properties", Journ. of Alloys and Compounds 1997, vol. 253, Iss May, pp. 44–50.

(Continued)

*Primary Examiner*—Hoa Q. Pham
(74) *Attorney, Agent, or Firm*—Steven J. Hultquist; Yongzhi Yang; Marianne Fuierer

(57) ABSTRACT

A hydrogen gas detector for detection of hydrogen gas in a gaseous environment. The detector comprises a light/heat source, an optical detector, and an optical barrier between the source and detector. The optical barrier responds to the presence of hydrogen by responsively changing from a first optical state to a different second optical state, whereby transmission of light from the light/heat source through the optical barrier is altered by the presence of hydrogen and the altered transmission is sensed by the optical detector to provide an indication of the presence of hydrogen gas in the gaseous environment.

42 Claims, 7 Drawing Sheets

U.S. PATENT DOCUMENTS

| | | | | | |
|---|---|---|---|---|---|
| 6,573,536 | B1 | * | 6/2003 | Dry | 257/88 |
| 6,590,773 | B1 | * | 7/2003 | Lin | 361/704 |
| 6,596,236 | B2 | * | 7/2003 | DiMeo et al. | 422/88 |
| 6,637,253 | B2 | * | 10/2003 | Dean et al. | 73/23.2 |
| 6,691,554 | B2 | * | 2/2004 | Eastman et al. | 73/25.03 |

OTHER PUBLICATIONS

Vajda–P, "Hydrogen ordering and metal semiconductor transitions in superstoichiometric rare–earth dihydrides" Journ. of Alloys and Compounds, 1995, vol. 231, Iss 1–2, pp. 170–175.

Huiberts–JN et al., "Synthesis of yttrium hydride films for ex–situ measurements", Journ. of Alloys and Compounds 1996, vol. 239, Iss 2, pp. 158–171.

J.N. Huiberts, R. Griessen J.H. Rector, R.J. Wijngaarden, J.P. Dekker, D.G. de Groot, N.J. Koeman, Nature 1996, vol. 380, Iss 6571, pp. 231–234.

Wang, X.W., et al, "Nature of the Insulating State in LaH3", Physical Review B–Condensed Matter 1997, vol. 56, Iss 12, pp. R7049–R7052.

Rehmof, A., et al., "Reversible loading of epitaxial Y(00.1) films with hydrogen", Physical Review B–Condensed Matter 1997, vol. 56, Iss 6, pp. R2897–R2899.

Kelly, P.J., et al, "Theoretical prediction of the structure of insulating Yh3", Physical Review Letters 1997, vol. 78, Iss7, pp. 1315–1318.

Reisfeld G., et al, "Hydrogen absorption by thin Pd/Nb films deposited on glass", Physical Review B–Condensed Matter 1996, vol. 53, Iss 8, pp. 4974–4979.

Vajda, P. in Handbook on the Physics and Chemistry of Rare Earths, vol. 20 (eds Gschneidner, K.A.; Eyring, L.) Amsterdam, Elsevier, 1995, pp. 207–291.

Mueller, W.M.;Blackledge, J.P.; Libowitz, G.G. in Metal Hydrides (eds Mueller, W.M.;Blackledge,J.P.; Libowitz, G.G.) New York, Academic, 1968, Ch. 9 & 10.

Encyclopedia of Inorganic Chemistry, ed. R. Bruce King, John Wiley & Sons, NY, vol. 6, pp. 3010–3011.

Chenier, J.P. in Survey of Industrial Chemistry, New York, VCH, 1992, p. 60.

(M. Terrones et. al., MRS Bulletin, 24, 8, pp. 44, (1999)).

Evans, W.J.; Drummond, D.K.; Hanusa, T.P.; Doedens, R.J. Bis(1,3–dimethylcycloentadienyl)yttrium Complexes. Synthesis and X–ray Crystallographic Characterization of [(1, 3–Me$_2$C$_5$H$_3$)$_2$ Y ($\mu$–Me)]$_2$, [(1,3–Me$_2$C$_5$H$_3$)$_2$ Y($\mu$–Me)]$_3$, and [(1,3–Me$_2$C$_5$H$_3$)$_2$(THF)Y($\mu$–Me)]$_2$, organometallics 1987, vol.6, pp. 2279–2285.

Jeske, G.; Lauke, H.; Mauermann, H.; Swepston, P.N.; Schumann, H.; Marks, T.J., "Highly Reactive Organolanthanides. Systematic Routes to and Olefin Chemistry and Late Bis(pentamethylcyclopentadienyl) 4f Hydrocarbyl and Hydride Complexes", J. Am. Chem. Soc.1985, vol. 107, pp. 8091–8103.

Wilkinson, G.; Birmingham, J.M., "cyclopentadienyl Compounds of Sc, Y, La, Ce and Some Lanthanide Elements", J. Am. Chem. Soc.1954 vol. 76, p. 6210.

Wayda, A.L., "Mono–, bis– and tris(t–butylcyclopentadienyl)lanthanoid Complexes", J. Organomet. Chem.1989, vol. 361, p. 73.

Tsutsui, M.; Gysling, H.J., "A New Series of Organolanthanides: Ln(indenyl)$_3$", J. Am. Chem. Soc.1969, vol. 91, pp. 3175–3178.

Schulz, D.L.; Hinds, B.J.; Neumayer, D.A.; Stern, C.L.; Marks, T.J. . , "Barium B –Ketoiminate Complexes Containing Appended Ether Lariats. Synthesis, Characterization, and Implementation as Fluorine Free Barium MOCVD Precursors", Chem. Mater.1993, vol. 5, pp. 1605–1617.

McGeachin, S.G., "Synthesis and Properties of Some B–Diketimines Derived From Acetylacetone, And Their Metal Complexes", Can. J. Chem.1968, vol. 46, pp. 1903–1912.

Van Buskirk, P.C.;Kirlin, P.S. . , "BaTiO$_3$—SrTiO$_3$ DRAM's Final Report", Phase I Final Report, Contract #DNA001–91–C–0078, Feb. 1991.

Zhang, J.; Gardiner, R.; Kirlin, P.S., Layered Superconductors: Fabrication, Properties and Applications, ed. D.T. Shaw and T.R. Schneider, MRS Proceedings, 1992, vol. 275, p. 419.

J.S. Suehle, et al., "Tin oxide gas sensor fabricated using CMOS micro–hotplates and in situ processing," IEEE Electron Device Lett, vol. 14, 1993, pp. 118–120.

Semancik et al., "the use of surface and thin film science in the development of advanced gas sensors," Appl. Surf. Sci., vol. 70. 1993, pp. 337–346.

R.E. Cavicchi, et al., "Fast temperature programmed sensing for microhotplate gas sensors," IEEE Electron Device Letters, vol. 16, 1995, pp. 286–288.

R.E. Cavicchi, et al., "Growth of SnO$_2$films on micromachined hotplates," Appl. Phys. Lett., vol. 66, 1995, pp. 812–814.

F.J.A. den Broeder, et al., "Visualization of hydrogen migration in solids using switchable mirrors," Nature vol. 394, 1998, pp. 656–658.

Van der Sluis, et al., "Optical switches based on magnesium lanthanide alloy hydrides," Appl. Phys. Lett., vol. 70, 1997, pp. 3356–3358.

J.N. Huiberts et al., Logarithmic divergence of the electrical resistivity in the metal hydride YH3–d, Physical Review Letters vol. 79, 1997, pp. 3724–3727.

Kremers, N.J. et al., "Optical transmission spectroscopy of switchable yttrium hydride films" Physical Review B, vol. 57, 1998, pp. 4943–4949.

Bhandari, "Phase Change Materials Lead to Hydrogen Sensors," Sensor Technology, vol. 13, No. 5, May 1997, p. 7–8.

Yannopoulos, L.N.; Edwards, R.K.; Wahlbeck, P.G., "The Thermodynamics of the Yttrium–Hydrogen System", J. Phys. Chem.1965, vol.69, pp. 2510–2515.

Ahuja, R.; Johansson, B.; Wills, J.M.; Eriksson, O. "On the Semiconducting State and Structural Properties of YH$_3$ from First: Principles Theory"" Appl. Phys. Lett., 1997, vol. 71, No. 24, pp. 3498–3500.

Notten, P.H.L.; Kremers, M.; Griessen, R., "Optical Switching of Y–Hydride Thin Film Electrodes", J. Electrochem. Soc.1996, vol. 143, No. 10, pp. 3348–3353.

Vourvoulias, B.; Kwon, B., "Now You See it", Newsweek, 1998, Mar. 2, 1998, p. 13.

Freemantle, M., "Hydride Films Display Mirror–Window Changes", C&EN, 1996, p. 9.

(Walheim, S., Macromolecules, 30, pp.4995–5003 (1997)).

(Maurice Morton, Anionic Polymerization: Principles And Practice, pp.211, Academic Press, New York, New York (1993)).

Xiaodong Wang, et al., "Monolithic thin–film metal–oxide gas–sensor arrays with application to monitoring of organic vapors", Sensors 'and Actuators B 28, (1995) pp. 63–70.

C. Jeffrey Brinker, George W. Scherer Sol–Gel Science, "The Physics and Chemistry of Sol–Gel Processing" (Entire Book) "NOT FURNISHED".

* cited by examiner

OPTICAL HYDROGEN DETECTOR

CROSS REFERENCE TO RELATED APPLICATIONS

This is a continuation-in-part to application Ser. No. 09/442,568, filed on Nov. 18, 1999, now pending incorporated by reference in its entirety.

This invention was made with Government support under Contract No. NAS10-98027 awarded by the National Aeronautics and Space Administration. The Government has certain rights in this invention.

BACKGROUND OF THE INVENTION

1. Field of the Invention

The present invention generally relates to the detection of hydrogen gas in a gaseous environment, and more specifically to an optical hydrogen gas detector apparatus and hydrogen gas detection method.

2. Background of the Invention

Hydrogen holds vast potential as a commercial source of energy. As reported by the Hydrogen Technology Advisory Panel, (HTAP), "[h]ydrogen will join electricity in the $21^{st}$ Century as a primary energy carrier in the nation's sustainable energy future" (Vision Statement, The Green Hydrogen Report; The 1995 Progress Report of the Secretary of Energy's Hydrogen Technology Advisory Panel, DOE/GO-10095-179 May 1995). The abundance and versatility of hydrogen suggests that it can provide solutions to problems encountered with current fossil fuel energy systems, such as declining domestic supplies, air pollution, global warming, and national security.

Significant research and development efforts are currently underway to make the widespread use of hydrogen technically and economically feasible. These efforts are directed toward creating the basic infrastructure of a hydrogen economy: production, storage, transport and utilization. An underlying need of each of these infrastructural components is the ability to detect and quantify the amount of hydrogen gas present in a gaseous environment. This is critical not only for health and for human safety reasons, but will be required as a means of monitoring hydrogen-based technology and for the development of high-efficiency hydrogen processes. Hydrogen gas sensors that can quickly and reliably detect hydrogen over a wide range of oxygen and moisture concentrations are not currently available, and must be developed in order to facilitate the transition to a hydrogen-based energy economy.

Hydrogen is the lightest and most abundant element in the universe. As a gas, hydrogen is odorless, colorless, and burns with a virtually invisible flame (an effective odorant and luminant with minimal system and emission impact has not yet been developed). It has a lower explosive limit (LEL) of 4% in air, and an upper explosive limit (UEL) of 75%. The minimum self-ignition temperature of a stoichiometric mixture of hydrogen and oxygen is 585° C.

Although the safety record of the commercial hydrogen industry has been excellent, it is estimated that undetected leaks were involved in 40% of industrial hydrogen incidents that did occur ("The Sourcebook for Hydrogen Applications," by the Hydrogen Research Institute and the National Renewable Energy Laboratory, 1998). Emerging hydrogen-based energy systems will require hydrogen sensors that are as ubiquitous as computer chips have become in current home, office, factory and vehicular environments. This circumstance in turn requires that massive numbers of hydrogen sensors be readily manufacturable at low cost.

In this respect, any commercially viable hydrogen detector must satisfy the following requirements:
the detector must be selective to hydrogen in a wide variety of gaseous environments, including oxygen-rich, high-humidity environments found in fuel cells;
the detector must have a good signal-to-noise ratio and a large dynamic range;
the detector should minimize both failures to detect and false positives;
the detector must operate rapidly, inasmuch as high speed detection is a critical requirement to ensure rapid response to potentially hazardous leaks of hydrogen;
the detector must have a long lifetime between calibrations, in order to minimize maintenance requirements and achieve low lifetime costs with high reliability;
the detector must be characterized by low power consumption, which is particularly critical for portable instrumentation and personnel monitoring device applications;
the hydrogen detector should be characterized by a high level of operational safety, and should not depend on any heated wire, open flame, or spark for its operation; and
the hydrogen detector must be reliably and reproducibly manufacturable at high volumes, and be readily available in great numbers, at low cost, to achieve ubiquitous monitoring of numerous, dynamically changing and diverse environments.

SUMMARY OF THE INVENTION

The present invention relates in one aspect to a hydrogen gas detector for detection of hydrogen gas in a gaseous environment, such detector comprising a light/heat source, an optical detector, and an optical barrier between the source and detector, wherein the optical barrier responds to the presence of hydrogen by responsively changing from a first optical state to a different second optical state, whereby transmission of light from the light/heat source through the optical barrier is altered by the presence of hydrogen and the altered transmission is sensed by the optical detector to provide an indication of the presence of hydrogen gas in the gaseous environment.

In another aspect, the invention relates to a hydrogen gas detector, comprising
 a light source;
 a thermal energy source;
 an optical filter having an optical transmissivity responsive to the presence and concentration of hydrogen gas in an ambient environment to which the optical filter is exposed, such optical filter being disposed in proximity to the light source so that the optical filter is illuminated with light from the light source, and being operatively coupled to the thermal source so that the optical filter is heated by the thermal source;
 a light detector generating an output signal, the state of such output signal being proportional to the intensity of light impinging on the light detector, and the light detector being disposed in light-sensing relationship to the optical filter, whereby light from the light source passing through the optical filter impinges on the light detector and generates the output signal as an indication of the presence and/or concentration of hydrogen gas in the ambient environment.

A further aspect of the invention relates to a hydrogen detection system for monitoring an extended or remote area region for the incursion or generation of hydrogen therein. The hydrogen detection system comprises a multiplicity of hydrogen gas detector elements each of which (i) is arranged for exposure to a specific individual locus of the extended area region and (ii) employs an optical filter comprising a rare earth metal thin film that exhibits a detectable change in optical transmissivity when the rare earth metal thin film is contacted with hydrogen at such locus.

A further aspect of the invention relates to a method of fabricating a hydrogen gas detector, comprising:

providing a source of luminous and thermal energy including an output surface for emitting light and thermal energy;

depositing on the output surface an optical filter comprising a rare earth metal thin film that responds to contact with hydrogen by exhibiting a detectable change of optical transmissivity;

positioning a light detector in light-sensing proximity to the source of luminous and thermal energy, whereby a change in optical transmissivity of the rare earth metal thin film in exposure to hydrogen gas is detected as a change in luminous energy flux impinging on the detector, and outputting a signal indicative of the change in luminous energy flux.

Other aspects, features and embodiments of the invention will be more fully apparent from the ensuing disclosure and appended claims.

DETAILED DESCRIPTION OF THE INVENTION AND PREFERRED EMBODIMENTS THEREOF

Figure 1A:
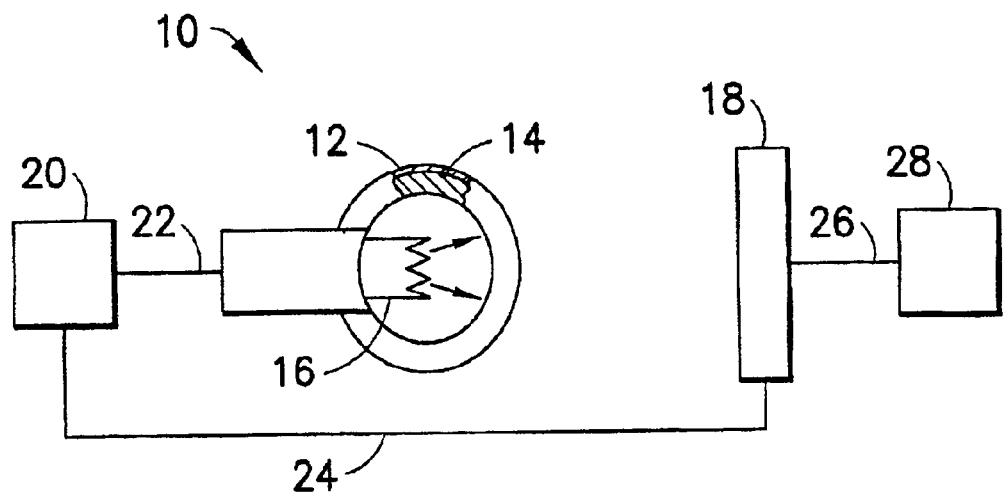
FIG. 1A is a schematic representation of the present invention according to one embodiment, in the absence of hydrogen gas.

The disclosure of U.S. patent application Ser. No. 09/042, 698 filed Mar. 17, 1998 in the names of Gutam Bandari and Thomas H. Baum for "Hydrogen Sensor Utilizing Rare Earth Metal Thin Film Detection Element" is hereby incorporated herein by reference in its entirety.

The present invention utilizes a light/heat source, an optical detector, and an optical barrier between the source and detector. The optical barrier responds to the presence of hydrogen and transitions from a first optical state, e.g., a state of optical opacity, in the absence of hydrogen to a second and different optical state, e.g., a state of optical translucency/transparency in the presence of hydrogen.

In general, the optical barrier may comprise any suitable material whose optical transmissivity characteristics are hydrogen-dependent, being in one of different optical states dependent on the presence or absence of hydrogen. By way of specific example, the hydrogen-sensitive optically variable material may comprise a rare earth metal thin film of the type disclosed in the aforementioned U.S. patent application Ser. No. 09/042,698, optionally overcastted with a hydrogen-permeable protective layer such as palladium. The optically variable character of rare earth metal films is based on the reversible, hydrogen-induced transition from the metallic dihydride compound to the semiconducting trihydride compound. For example, in the case of yttrium, this transition is represented by the following equation involving yttrium:

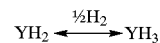

wherein the dihydride compound is optically opaque in thin film form, and the trihydride is optically transparent in thin film form.

As used herein, the term "rare earth metal thin films" will be understood as broadly referring to thin films (e.g., films having a thickness of less than about 1,000 microns) of rare earth metals of the Periodic Table having the atomic numbers of 51 to 71 inclusive, which are capable of existing in divalent as well as trivalent hydride forms, as well as yttrium. Of the rare earth metals in the lanthanide series of the Periodic Table, lanthanum is particularly preferred. While yttrium is not technically a rare earth metal, it is included because thin films of yttrium exhibit properties similar to those of thin films of rare earth metals (having the atomic numbers of 51 to 71 inclusive) of the Periodic Table.

In the use of rare earth metal thin films in the practice of the invention for hydrogen detectors, in applications in which the thin film will or may encounter oxidizing species in the environment being monitored for hydrogen, such as oxygen, moisture (relative humidity), nitrogen oxides, carbon oxides, etc., it is advantageous to coat or encapsulate the rare earth metal thin film with a hydrogen-permeable protective material that prevents such oxidizing species from contacting the rare earth metal thin film.

The protective material may for example absorb oxygen and allow diffusion of hydrogen through the protective material to the rare earth metal thin film. Alternatively, the protective material may be impermeable to oxygen and/or other oxidizing species.

The protective material when present as an overlayer coating or encapsulate should be continuous and atomically dense in order to provide an effective barrier against oxidation. The thickness of the overlayer may be readily selected to minimize oxygen permeation while maximizing the response of the rare earth metal thin film to hydrogen.

In one embodiment of the present invention in which a protective material overlayer is employed, the overlayer may be formed of a noble metal such as Pd, Pt, or Ir, or alloys or combinations thereof with one another or with other metal species. Particularly useful alloys for such protective material overlays include Pd—Ag and Pd—Ni.

Any suitable forming or deposition process may form the rare earth metal thin film. For example, the rare earth metal thin film may be formed by chemical vapor deposition, physical vapor deposition, solution deposition, electroplating, electroless plating, sputtering, pulsed laser deposition or any other suitable technique or methodology for formation or deposition thereof. The rare earth metal film may be formed on any suitable substrate, e.g., silicon, silicon oxide, silicon carbide, alumina, vitreous or ceramic materials, etc.

A particularly preferred technique for forming the rare earth metal thin film in the broad practice of the present invention is chemical vapor deposition (CVD). Due to its high throughput and low cost, the CVD process is advantageous in fabricating sensor devices of the present invention in an efficient and economic manner. The ability of CVD to conformably coat substrates provides further benefit in the deposition of a protective overlayer material, in instances where the hydrogen sensor of the invention is fabricated with such a barrier material for preventing the reaction of the rare earth metal with oxidizing species in the environment being monitored for hydrogen.

The CVD process may utilize bubbler delivery or liquid delivery with subsequent flash vaporization, using a suitable rare earth metal precursor or source compound, to generate a precursor vapor which is transported to a heated substrate for decomposition to form the desired rare earth metal film. Such precursors must be robust and volatile at the temperature of vaporization, yet they must decompose cleanly and efficiently on the substrate.

Suitable precursors may be readily determined within the skill of the art by screening techniques conventionally used in the art of CVD formation of thin films, including thermogravimetric analysis (TGA) and differential scanning calorimetry (DSC) analysis.

The light/heat source used in the hydrogen detector of the present invention may comprise any suitable source of both luminescent and thermal energy, either together or separately. The light source may for example comprise an incandescent bulb, LED, fluorescent tube, electroluminescent lamp, or laser. The heat source may for example comprise a resistive wire (including the filament of an incandescent bulb); an exothermic chemical reaction; ultrasonic, acoustic, microwave, laser, or other directed radiation; or the like.

The optical detector used in the practice of the present invention may likewise comprise any suitable detector as known in the art, such as a photodiode, scintillation detector, photomultiplier tube, etc. The optical detector can be of structural or electrical/electronic character, or the optical detector may otherwise comprise the human eye.

In one preferred embodiment of the present invention, the light/heat source comprises a miniature incandescent light bulb, and the hydrogen-sensitive optical barrier is a rare earth metal thin film coating deposited directly on the surface of bulb.

In the absence of hydrogen, light generated from the bulb filament is blocked from the detector by the opaque rare earth metal thin film. In the presence of hydrogen, the coating partially transforms to a transparent trihydride state, becoming translucent in overall character and thus light-transmissive in effect. Light can thus pass through the coated bulb and reach the detector, so that the occurrence of light transmission is indicative of the presence of hydrogen.

The optical detector may be electrical or electronic in character, and may be constructed and arranged to provide a suitable output. Further, by appropriate calibration, and correspondingly sensitive detector componentry, the concentration of hydrogen in the environment being monitored can be determined quantitatively, and outputted to a use of the detector.

In the embodiment described above, wherein a rare earth metal thin film is coated on a light source concomitantly with the production of light producing heat, the thermal energy generated by the light source will heat the rare earth metal thin film coating, thereby minimizing the "recovery" time necessary for the rare earth metal thin film to "reverse-transition" from the transparent tri-hydride form incident to hydrogen exposure, to an opaque dihydride upon removal of hydrogen gas and/or the detector from the environment in which the detector was initially exposed to hydrogen.

In the above-described embodiment, featuring a hydrogen-sensitive film on a thermally emissive light source, the amount of light transmitted will be, in general, a function of the concentration of hydrogen present. This feature permits the detector of the present invention to be employed as a rudimentary hydrogen concentration measurement device, which as mentioned hereinabove can be calibrated to provide quantitative information about the hydrogen present in the gaseous environment being monitored. Alternatively, this concentration-dependent character of the optical transmissivity of the thin film material allows particular detectors to be engineered or adjusted for sensitivity to specific concentrations of hydrogen.

The present invention thus contemplates a hydrogen gas detector for detection of hydrogen gas in a gaseous environment. The detector simply and conveniently comprises a light/heat source, an optical detector, and an optical barrier between the source and detector. The optical barrier responds to the presence of hydrogen by responsively changing from a first optical state to a different second optical state, whereby transmission of light from the light/heat source through the optical barrier is altered by the presence of hydrogen. The resultant altered transmission is sensed by the optical detector to provide an indication of the presence of hydrogen gas in the gaseous environment.

The first optical state suitably comprises a state of optical opacity of the optical barrier, while the second optical state comprises a state of optical non-opacity of the optical barrier, e.g., a state of translucency/transparency of the optical barrier. The optical barrier suitably comprises a rare earth metal thin film, such as an yttrium thin film, optionally overlaid by a protective film that is permeable to hydrogen gas such as a palladium film.

The hydrogen gas detector of the invention may be usefully embodied as a unitary portable article, e.g., comprising a power supply such as a battery. The hydrogen gas detector may suitably incorporate an output module operatively coupled to the optical detector, and arranged to provide an output alarm indicative of the presence or concentration of hydrogen gas in the gaseous environment, e.g., a visual, audible or tactile alarm.

The light/heat source of the detector in a simple embodiment comprises a lamp element providing heat output incident to the generation of light, such as an incandescent lamp. The incandescent lamp may be formed in a conventional manner as including a light-transmissive bulb, on an exterior surface of which is coated a rare earth metal thin film as the optical barrier. Such hydrogen gas detector may be of a very compact form, e.g., of a hand-held size and character, wherein the light/heat source comprises a lamp element providing heat output incident to the generation of light, with an yttrium thin film coated on the lamp element as the optical barrier, and a protective palladium film coated on the yttrium thin film.

The hydrogen gas detector of the invention may be operatively coupled with corresponding hydrogen gas detectors to form an extended area monitoring system for detection of hydrogen gas in the gaseous environment of such extended area. For example, a hydrogen detection system for monitoring an extended or remote area region for the incursion or generation of hydrogen therein, may suitably comprise a multiplicity of hydrogen gas detector elements each of which (i) is arranged for exposure to a specific individual locus of the extended area region and (ii) employs an optical filter comprising a rare earth metal thin film that exhibits a detectable change in optical transmissivity when the rare earth metal thin film is contacted with hydrogen at such locus.

The hydrogen gas detector of the invention may therefore include in an illustrative embodiment the following components: (i) a light source; (ii) a thermal energy source; (iii) an optical filter having an optical transmissivity responsive to the presence and concentration of hydrogen gas in an ambient environment to which the optical filter is exposed, such optical filter being disposed in proximity to the light source so that the optical filter is illuminated with light from the light source, and being operatively coupled to the thermal source so that the optical filter is heated by the thermal source; and (iv) a light detector generating an output signal, wherein the state of the output signal is proportional to the intensity of light impinging on the light detector. The light detector is suitably disposed in light-sensing relationship to the optical filter, whereby light from the light source passing through the optical filter impinges on the light detector and generates the output signal as a indication of the presence and/or concentration of hydrogen gas in the ambient environment.

In the hydrogen gas detector of the invention, the source of luminous energy may be a light-generating element selected from among incandescent bulbs, light emitting diodes, fluorescent lamps, electroluminescent lamps, and optical lasers. The thermal energy source may be a heat-generating element such as an incandescent bulb, resistive wire, exothermic chemical reaction, ultrasonic radiation, acoustic radiation, microwave radiation, or laser radiation.

The light source and the thermal energy source may comprise a same element, or alternatively the light source and the thermal energy source may comprise different elements.

The light detector may comprise any suitable light detection elements, e.g., photodiodes, avalanche photodiodes, phototubes, photomultiplier tubes, microchannel plates, solar cells, image intensifiers, photoconductor detectors, charge-coupled devices, or combinations or arrays thereof.

The optical filter preferably comprises a rare earth metal thin film deposited on an optical output surface of the light source. The rare earth metal thin film may comprise a rare earth metal component selected from the group consisting of trivalent rare earth metals reactive with hydrogen to form both metal dihydride and metal trihydride reaction products, wherein the metal dihydride and metal trihydride reaction products have differing optical transmissivity.

The rare earth metal thin film suitably comprises at least one metal selected from the group consisting of:
scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, and lawrencium,
alloys thereof, and
alloys containing one or more of such metals alloyed with an alloying component selected from the group consisting of magnesium, calcium, barium, strontium, cobalt and iridium.

Most preferably, the rare earth metal thin film comprises yttrium.

The rare earth metal thin film may optionally be overlaid by a hydrogen-permeable material comprising a metal such as Pd, Pt, Ir, Ag, Au, Ni, Co, or an alloy thereof. The rare earth metal thin film may also optionally be overlaid by a hydrogen-permeable material that is doped with a dopant, e.g., Mg, Ca, Al, Ir, Ni or Co.

Preferred overlay metals include palladium, platinum, and iridium.

The hydrogen gas detector may be fabricated by the following sequence of steps:

First, a source of luminous and thermal energy is provided. Such source includes an output surface for emitting light and thermal energy. Next, an optical filter is deposited on the output surface. The optical filter comprises a rare earth metal thin film that responds to contact with hydrogen by exhibiting a detectable change of optical transmissivity.

Next, a light detector is positioned in light-sensing proximity to the source of luminous and thermal energy, whereby a change in optical transmissivity of the rare earth metal thin film in exposure to hydrogen gas is detected as a change in luminous energy flux impinging on the detector, to output a signal indicative of the change in luminous energy flux. Such output may be of any suitable type, e.g., visual outputs, optical outputs, tactile outputs, electrical outputs and/or auditory outputs.

The rare earth metal thin film may be formed on the output surface of the source of luminous and thermal energy, by a technique such as physical vapor deposition, chemical vapor deposition, sputtering, solution deposition, focused ion beam deposition, pulsed laser deposition, electrolytic plating, or electroless plating.

In one embodiment, the rare earth metal thin film is formed on the substrate by chemical vapor deposition using an organometallic precursor that thermally decomposes to the metal hydride or elemental metal in a reducing environment of hydrogen.

The rare earth metal thin film in the practice of the invention advantageously comprises at least one metal selected from among the following:
scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, and lawrencium,
alloys thereof, and
alloys containing one or more of such metals alloyed with an alloying component selected from the group consisting of magnesium, calcium, barium, strontium, cobalt and iridium.

The rare earth metal thin film suitably comprises a rare earth metal component selected from the group consisting of trivalent rare earth metals reactive with hydrogen to form both metal dihydride and metal trihydride reaction products, wherein the metal dihydride and metal trihydride reaction products have differing optical transmissivity, and wherein transitions between the metal dihydride and metal trihydride reaction products are caused by the presence or absence of hydrogen gas contacting the rare earth metal thin film, e.g., a rare earth metal thin film overlaid by a hydrogen-permeable material, such as Pd, Pt, Ir, Ag, Au, Ni, Co, or alloys thereof, and optionally doped with a dopant selected from the group consisting of Mg, Ca, Al, Ir, Ni and Co.

In one embodiment, the rare earth metal thin film is formed of a metal such as lanthanum or yttrium, and the rare earth metal thin film is formed on the output surface of the light/heat source by CVD utilizing corresponding precursors, e.g., tris(cyclopentadienyl)lanthanum, tris(cyclopentadienyl)yttrium, β-diiminate complexes of lanthanum, β-diiminate complexes of yttrium; lanthanum amides, and yttrium amides.

When the rare earth metal thin film comprises lanthanum, the rare earth metal thin film preferably is formed on the substrate by CVD utilizing a precursor such as $La(NR_2)_3$, $La(NR_2)_3.L$, $La(R)_3$ or $La(R)_3.L$ wherein R is $C_1$ to $C_8$ alkyl or $C_1$ to $C_8$ aryl and L is a Lewis base ligand selected from the group consisting of amines, aryls and aryl amines, more specifically, NH3, primary amines, secondary amines, tertiary amines, polyamines, and more specifically, pyridine, methylamine, dimethylamine trimethylamine, dimethylethylamine, N,N,N',N'-tetramethylethylenediamine and N,N,N',N',N''-pentamethyldiethylenetriamine and such Lanthanum precursor may be deposited in the presence of a reducing and/or inert gas, e.g. $NH_3$, $NH_3/H_2$ or $NH_3/N_2$.

When the rare earth metal thin film comprises yttrium, the rare earth metal thin film may be formed on the substrate by CVD utilizing a precursor, such as $Y(NSiR'_3)_3$, wherein each of R' may be same or different and are independently selected from the group consisting of $C_1$ to $C_8$ alkyl or $C_1$ to $C_8$ aryl.

When palladium is utilized as an overlayer material, the overlayer may be formed by chemical vapor deposition on the rare earth metal thin film, using a palladium precursor such as $Pd(hfac)_2$, $Pd(allyl)_2$, $Pd(allyl)(hfac)$, Pd(methylallyl)(hfac), CpPd(allyl) or $COD.Pd(Me)_2$.

Figure 2:
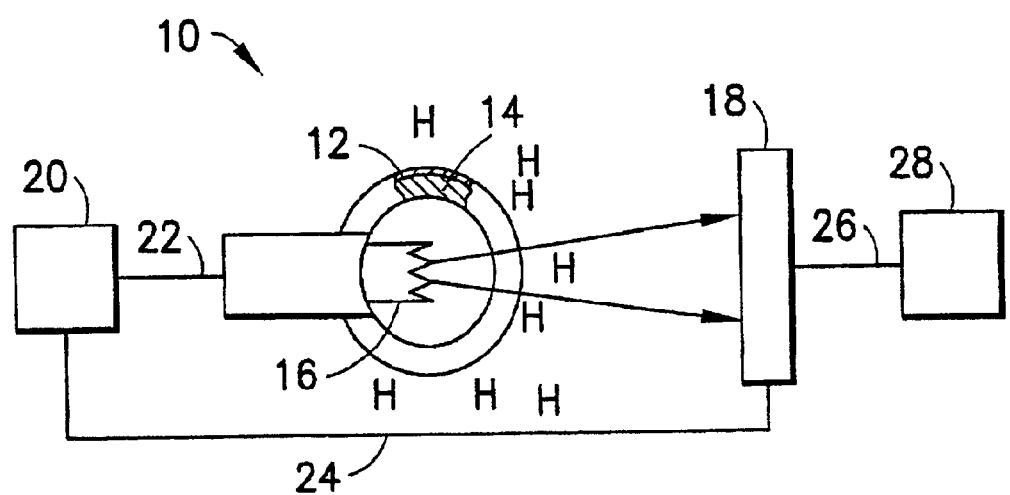
FIG. 2 is a schematic representation of the present invention according to one embodiment, in the presence of hydrogen gas.

An illustrative embodiment of the present invention is depicted in FIGS. 1 and 2, wherein like components are correspondingly numbered for ease of reference.

Referring to FIG. 1A, light bulb 10 comprising incandescent filament 16 has deposited thereon a rare earth metal thin film layer 12, preferably comprising a trivalent rare earth metal such as yttrium, that is reversibly reactive with hydrogen to form both metal dihydride and metal trihydride reaction products. Over the rare earth metal thin film layer 12 is deposited a protective layer 14, comprising a suitable material, such as for example Pd, Pt, Ir, Ag, Au, Ni, Go, or alloys thereof, and most preferably comprising palladium. In the absence of hydrogen in the ambient environment to which the bulb is exposed, the rare earth metal thin film 12 is in a metallic, optically reflective dihydride state. Light from filament 16 is attenuated by the dihydride state of rare earth metal thin film layer 12 and thus only a portion of it reaches photo-detector 18.

The light bulb 10 is connected by power supply transmission wire 22 to a power supply 20. The power supply 20 is joined by power supply wire 24 to the photo-detector 18, to provide power to the latter. The photo-detector 18 is joined by output signal transmission wire 26 to output module 28, which may provide a visual, audible, tactile or other alarm indicative of the presence of hydrogen in the gaseous environment being monitored, or which may provide a quantitative output correlative of the concentration of hydrogen in the environment being monitored.

FIG. 2 shows hydrogen (denoted symbolically by multiple "H"s in the environs of the detector) present in the atmosphere to which coated light bulb 10 is exposed. The hydrogen diffuses through protective layer 14 and reacts with rare earth metal thin film layer 12. This causes portions of rare earth metal thin film 12 to transition to a semiconducting, optically transparent trihydride state. Some light from filament 16 thereby passes through the translucent rare earth thin film layer 12 to impinge on photo-detector 18, generating a signal transmitted in line 26 to the output module 28, corresponding to the presence and intensity of incident light.

Figure 1B:
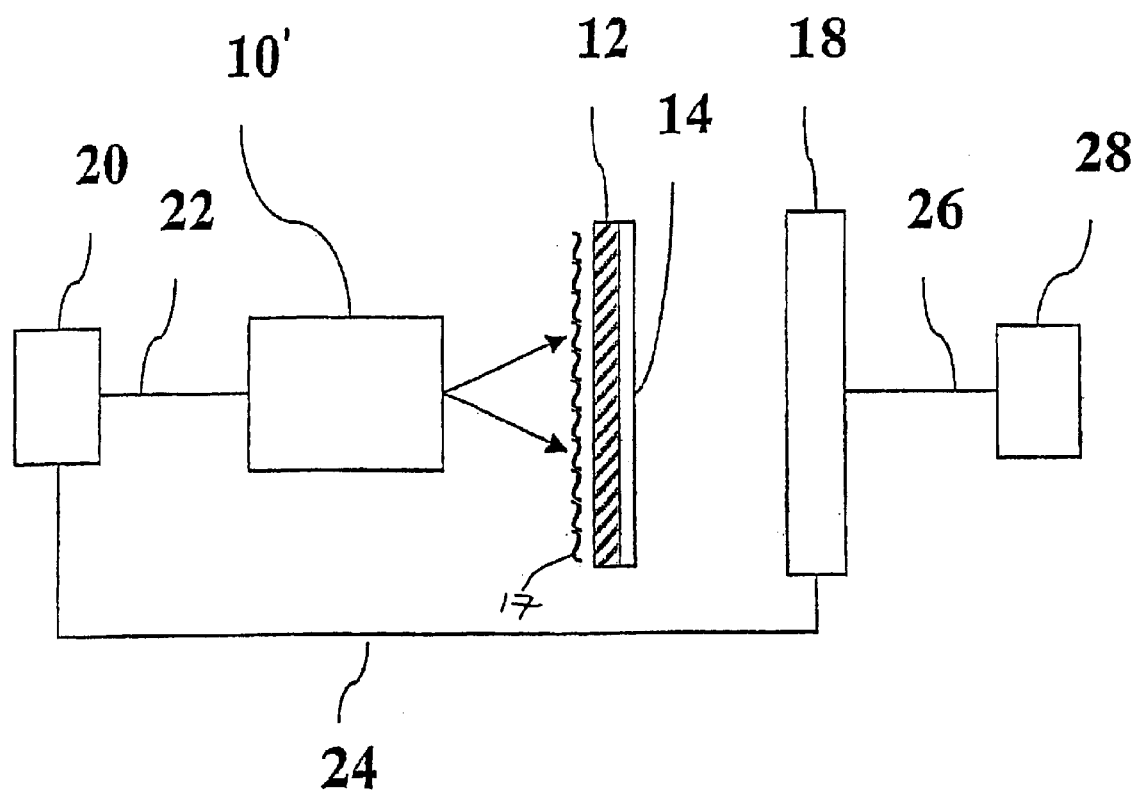
FIG. 1B is a schematic representation of the present invention according to a second embodiment, in the absence of hydrogen gas.

In FIG. 1A, filament 16 of coated light bulb 10 is additionally a heat source that provides thermal energy for elevating the temperature of rare earth thin film 12. In FIG. 1B, in contrast the light source 10' generates little or no thermal energy, and a separate heat-generating element 17 is provided as a heat source for supplying the necessary thermal energy for heating the rare earth thin film 12 to an elevated temperature. The separate heat-generating element 17 may comprise incandescent bulbs, resistive wires, exothermic chemical reactions, ultrasonic radiation, acoustic radiation, microwave radiation, laser radiation or other such heat-generating elements as known to those skilled in the art. Specifically, FIG. 1B depicts the heat-generating 17 as a resistive wire for exemplary and illustrative purposes, which is not intended to and should not be construed to limit the broad scone of the present invention. The transition of rare earth thin film 12 from reflective dihydride to transparent trihydride state and back, in response to the absence or presence, respectively, of hydrogen occurs much more rapidly at elevated temperatures. This reduces both the response time of the detector in the presence of hydrogen and its recovery to the opaque "null state" in the absence of hydrogen.

Figure 3:
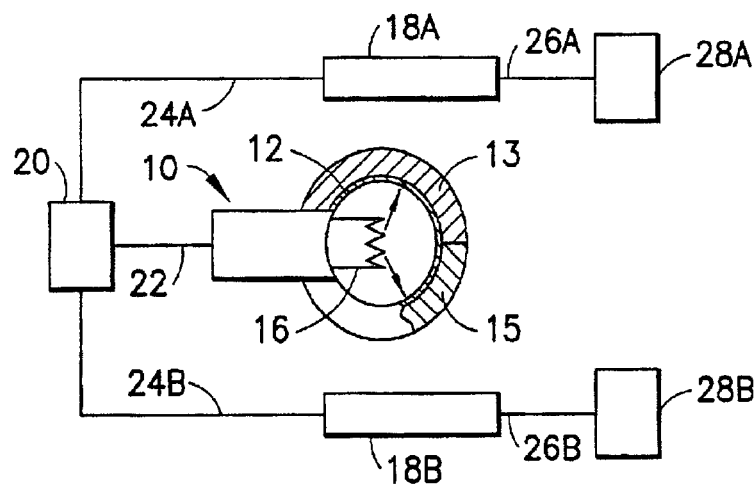
FIG. 3 is a schematic representation of the present invention according to a second embodiment, in the absence of hydrogen gas.
Figure 4:
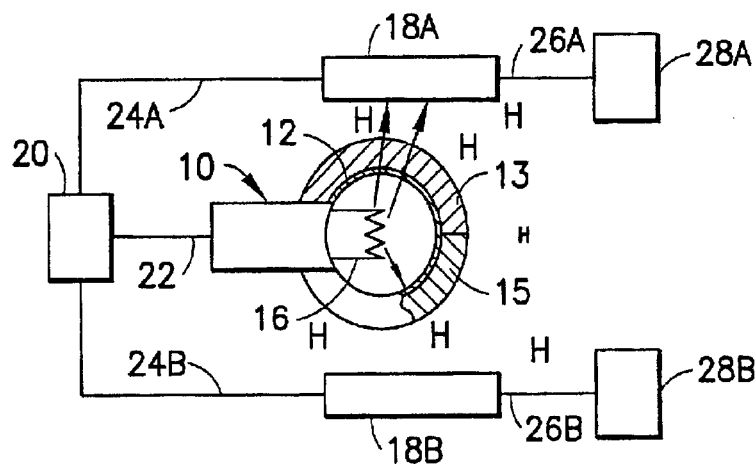
FIG. 4 is a schematic representation of the present invention according to a second embodiment, in a low concentration of hydrogen gas.
Figure 5:
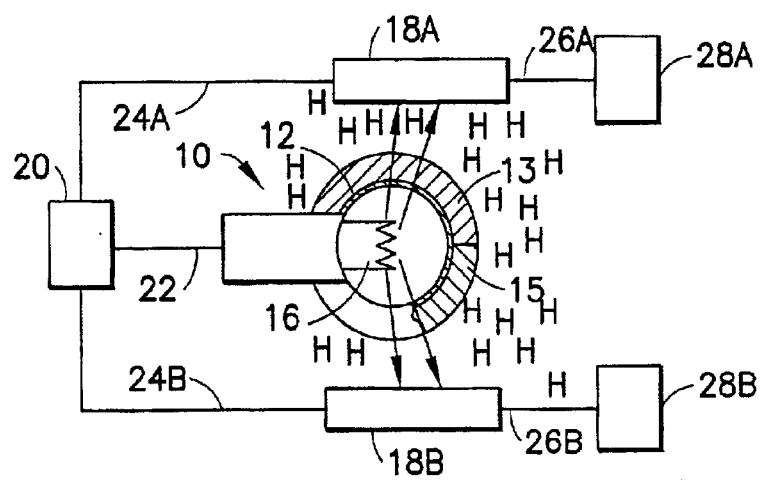
FIG. 5 is a schematic representation of the present invention according to a second embodiment, in a high concentration of hydrogen gas.

An alternative illustrative embodiment of the present invention is depicted in FIGS. 3, 4, and 5, wherein like components are correspondingly numbered with each figure and with FIGS. 1 and 2, for ease of reference. This embodiment demonstrates one manner in which different bulb coatings and multiple detectors may be employed to increase the dynamic range of the hydrogen gas detector.

FIG. 3 depicts light bulb 10 comprising incandescent filament 16 and having deposited thereon a rare earth metal thin film layer 12, preferably comprising a trivalent rare earth metal such as yttrium, that is reversibly reactive with hydrogen to form both metal dihydride and metal trihydride reaction products. Over the rare earth metal thin film layer 12, on approximately half of the optical output surface of the bulb, is deposited a protective layer 13, comprising a suitable material with a relatively high permeability to hydrogen, such as for example Pd, Pt, Ir, Mg, Ca, Ag, Au, Ni, Co, or alloys thereof, and most preferably comprising palladium. Over the rare earth metal thin film layer 12, on approximately the opposing half of the optical output surface of the bulb from protective layer 13, is deposited a protective layer 15, comprising a suitable material with a relatively lower permeability to hydrogen as compared to protective layer 13, such as for example Pt, Ir, Mg, Ca, Ag, Au, Ni, Co, or alloys thereof, and most preferably comprising Iridium. Arranged in light-receiving relationship with the side of coated bulb 10 corresponding to high hydrogen permeability protective layer 13 is photo-detector 18A. Similarly, photo-detector 18B is arranged in light-receiving relationship with the side of coated bulb 10 corresponding to low hydrogen permeability protective layer 15. In the absence of hydrogen in the ambient environment to which the bulb is exposed, the rare earth metal thin film 12 is in a metallic, optically reflective dihydride state. Light from filament 16 is blocked by the reflective dihydride state of rare earth metal thin film layer 12 and thus does not reach either photo-detector 18A or 18B.

The light bulb 10 is connected by power supply transmission wire 22 to a power supply 20. The power supply 20 is joined by power supply wire 24A to the photo-detector 18A, and by power supply wire 24B to the photo-detector 18B, to provide power to each photo-detector. The photo-detector 18A is joined by output signal transmission wire 26A to output module 28A, which may provide a visual, audible, tactile or other alarm indicative of the presence of hydrogen in the gaseous environment being monitored at a first concentration level corresponding to the relatively high hydrogen permeability of protective layer 13. Similarly, photo-detector 18B is joined by output signal transmission wire 26B to output module 28B, which may provide a visual, audible, tactile or other alarm indicative of the presence of hydrogen in the gaseous environment being monitored at a second concentration level corresponding to the relatively low hydrogen permeability of protective layer 15.

FIG. 4 shows a relatively low concentration of hydrogen (denoted symbolically by several "H"s in the environs of the detector) present in the atmosphere to which coated light bulb 10 is exposed. The hydrogen diffuses through high hydrogen permeability protective layer 13 and reacts with the half of rare earth metal thin film layer 12 that underlies it. This causes portions of that half of rare earth metal thin film 12 to transition to a semiconducting, optically transparent trihydride state. Some light from filament 16 thereby passes through that half of the translucent rare earth thin film layer 12 to impinge on photo-detector 18A, generating a signal transmitted in line 26A to the output module 28A, corresponding to the presence and intensity of incident light, and indicative of presence of hydrogen in the environment of bulb 10 of at least a first characteristic concentration. The relatively low concentration of hydrogen in the environment of bulb 10, together with the relatively low hydrogen permeability of protective layer 15, is insufficient to react enough hydrogen with the half of rare earth metal thin film layer 12 which underlies protective layer 15 to trigger a similar transition. This half of rare earth metal thin film layer 12 remains in a metallic, optically reflective dihydride state, and light from filament 16 is blocked from reaching photo-detector 18B. Thus, no signal is transmitted in line 26B to the output module 28B, indicating that the hydrogen gas present in the environment of bulb 10 (as indicated by output module 28A) is below a second characteristic concentration.

FIG. 5 shows a relatively high concentration of hydrogen (denoted symbolically by many "H"s in the environs of the detector) present in the atmosphere to which coated light bulb 10 is exposed. The hydrogen diffuses through both the high hydrogen permeability protective layer 13 and the low hydrogen permeability protective layer 15, and reacts with both halves of rare earth metal thin film layer 12. This causes portions of both halves of rare earth metal thin film 12 to transition to a semiconducting, optically transparent trihydride state. Some light from filament 16 thereby passes through both halves of the translucent rare earth thin film layer 12 to impinge on both photo-detector 18A and photo-detector 18B. Corresponding signals are transmitted in line 26A to the output module 28A, and in line 26B to the output module 28B, respectively. The visual, audible, tactile or other alarm present at both output modules 28A and 28B indicates the presence of hydrogen gas in the environment of bulb 10 of at least a second characteristic concentration.

Such a two-step hydrogen gas detector alarm may be advantageously employed where, for example, the low concentration alarm from output module 28A may serve as a warning, indicating investigation is warranted, while the high concentration alarm from output module 28B may indicate an unacceptable safety hazard, necessitating evacuation.

In yet another alternative embodiment, the dynamic range of hydrogen gas detection quantization may be expanded by employing a plurality of incandescent bulbs, and associated alarm-triggering photo-detectors, wherein each bulb is coated with a rare earth metal thin film layer, preferably comprising a trivalent rare earth metal such as yttrium, that is reversibly reactive with hydrogen to form both metal dihydride and metal trihydride reaction products. The rare earth metal thin film layer on each bulb may be overlaid by a protective layer, comprising a suitable material, such as for example Pd, Pt, Ir, Mg, Ca, Ag, Au, Ni, Co, or alloys thereof, wherein the hydrogen permeability of the protective layer on each bulb is selected and/or engineered to trigger a transition in the underlying trivalent rare earth metal thin film from a metallic, optically reflective dihydride state to a semiconducting, optically transparent trihydride state at or above a certain characteristic concentration of hydrogen gas in the environment of the coated bulb. Alternatively, or additionally, the transition characteristics of the various rare earth metal thin films in the array may be altered by operation of the bulbs at different light intensities and/or operating temperatures, and/or by altering the switching threshold of the photo-detectors. Within the broad practice of this embodiment of the present invention, the optimal number of bulb/photo-detector pairs, the characteristics of the variously engineered protective layers, the operating intensity of the incandescent bulbs, the switching threshold of the associated photo-detectors, and other system parameters may vary widely, depending on the application, and may be determined by one of ordinary skill in the art without undue experimentation.

In all of the above embodiments of the present invention, it is desirable to improve the speed and responsive of the rare earth metal thin films whose physical property changes in the presence of hydrogen gas are exploited to effect hydrogen gas detection. Applicants have discovered that the response time is strongly dependent on grain size, and that for a given grain size, an increase in surface roughness results in an increased speed of response, as compared to deposition on un-roughened substrates. Four methods of increasing the response time of the rare earth metal thin films by increasing the surface morphology roughness have been identified, and comprise alternate embodiments of the present invention. These four methods are: mechanical roughening; chemical roughening; deposition of roughened inorganic underlayers; and deposition of porous polymer underlayers, based on interpenetrating polymer networks.

Mechanical Roughening

There are several methods of mechanical roughening that can be used on substrates to increase the surface roughness of subsequently deposited rare earth noble metal bi-layer thin films. The first method uses abrasives, i.e. sand paper, metal files, polishing pads and polishing pastes or compounds. The substrate can be roughened to the desired finish through the choice of material, and choice of the grade, grit, or particle size. The abrasive can be a material such as $Al_2O_3$, SiC, or diamond based or any other suitably hard material. Another method of mechanical roughening is the use of a bead blasting technique, where again the final finish can be determined through the choice of the bead blasting material. These methods can be done in either a dry or a wet process. In wet processing, a number of fluids may be considered, such as water, mineral oil, or organic solvents.

Chemical Roughening

Chemical Roughening of the substrate can be achieved by dipping in an acid, such as HF, dilute HF, or buffered HF solution. In these methods, the amount of roughening will be determined by the type and concentration of the etchant, as well as the composition and initial roughness of the substrate. Chemical roughening may be applied sequentially to mechanical roughening to produce a desired morphology.

Deposition of Highly Exfoliated or Porous Inorganic Underlayers

This method is primarily founded on sol gel deposition of morphological rough $SiO_2$ or $Al_2O_3$ thin film layers. One method for achieving this is through the coating of the substrate with a TEOS/alcohol/acidified aqueous solution. The coating method controls thickness and uniformity of the film. The substrate may be dip coated, spray coated, or spin cast or lyophilized. The curing of this coating results in a porous or high surface area oxide thin film. The chemistry utilized in the sol-gel precursor stage and the drying techniques employed after the sol-gel is cast determine the porosity (microscopic to mesoporous), surface area (upwards of 900 $m^2$/g) and roughness of the thin film (Jeffrey Brinker, George Scherer, Sol-Gel Science: The Physics and Chemistry of Sol-Gel Processing, Academic Press, San Diego, Calif. (1990)). Subsequent deposition of rare earth noble metal bi-layer thin films onto the high area sol-gel will create a hydrogen sensitive device that is easily accessed by the gas of interest. The large diffusion coefficient of gases such as $H_2$ (0.84 $cm^2$/s at 295 K, 1 bar) insure that gaseous diffusion will not limit the response of the sensor.

Deposition of Porous Polymer Underlayers

Deposition of porous polymer underlayers, based on morphological control of interpenetrating, phase segregated, or copolymer polymers also allows one to achieve desirable high surface area structures for deposition of the active bi-metal layer.

Phase segregation of polymer mixtures from a common solvent has been used in anti-reflective coating methods (Walheim, S., *Macromolecules*, 30, pp.4995–5003 (1997)). A non-miscible polymer pair, such as PVC and polybutadiene, may be solvated at up to 5% weight in a common solvent, such as THF, and cast onto a surface to allow solvent evaporation upon which segregation of the polymer pair occurs. Dissolution of one of the polymer pair, polybutadiene, in a non-common solvent, hexane, leaves a porous PVC structure. Solvent, polymer pair, and molecular weight of the polymers all contribute to control the morphology.

Interpenetrating polymer networks from two part monomer or one part monomer-one part polymer systems also allow a controlled morphology to be synthesized which may subsequently be used as a high surface area thin film polymer film. For example, a methacrylate monomer and TEOS may be mixed in a common solvent, cast as a homogeneous thin film, and subsequently polymerized. Subsequent removal of one of the interpenetrating polymers will leave a highly porous film of the other polymer. For example, $SiO_2$, the product of TEOS polymerization, is readily removed with ½% anhydrous HF which would leave behind a polymethacrylate thin film network.

Nearly monodisperse copolymers manufactured from anionic polymerization of monomers whose polymers are non-miscible also exhibit phase segregation at the microscopic level. The radius of gyration of the polymer segments, solvent choice, and interfacial free energy of the bi-phase system determine the domain size and shape of the microstructure. A well known example uses a styrene-isoprene copolymer to produce regular arrays of anisotropically oriented tubes with nanometer dimensions (Maurice Morton, *Anionic Polymerization: Principles And Practice*, pp211, Academic Press, New York, N.Y. (1993)). Deposition of a bimetallic layer at high aspect ratios may be difficult in which case carbon nanotube research has demonstrated that small diameters possessing high surface tensions may promote capillary wetting of the microscopic tubes walls by a chemical route (M. Terrones et. al., *MRS Bulletin*, 24, 8, pp. 44, (1999)). For example, deposition of a CVD precursor from the bulk solvent may wet the walls of the nanoporous polymer film. The metal from the CVD precursor would subsequently be reduced followed by the second metal CVD precursor that would form the top layer of the bi-metal active material.

In still another embodiment of the present invention, the light and heat source for the hydrogen gas detector, as well as optionally the optical input to the photo-detector, may comprise fiber optics, quartz rods, or other optical waveguides. The trivalent rare earth metal thin film may, in such embodiment, be deposited directly on the optical output surface of the optical waveguide, or alternatively on a surface coupled in light-receiving relationship with the waveguide. Hydrogen gas detectors according to this embodiment of the present invention present significant advantages, including the ability to be conformably routed to many places where installation of incandescent bulbs would be impractical due to size or space considerations, or would present unacceptable safety risks.

To obtain satisfactorily rapid response/recovery time, the trivalent rare earth metal thin film must be heated. One means of accomplishing this in a fiber optics waveguide application is to construct a layered substrate at the optical output surface that would absorb optical energy at one wavelength, particularly in the IR region, but would transmit optical energy at a different wavelength (the wavelength of the associated detector). Thus, one high-intensity wavelength is used to heat the optical barrier, and a second wavelength provides the signal, or probe, directed at the optical detector.

One method of forming such a layered substrate, and one embodiment of the present invention, is through sol gel deposition of morphological rough $SiO_2$ or $Al_2O_3$ thin film layers as described above. Subsequent deposition of rare earth noble metal bi-layer thin films onto the sol-gel will create unitary light/heat source and optical barrier with selective light transmission properties dependent upon the concentration of hydrogen gas in the region of the thin film.

Another way to utilize one wavelength of a polychromatic light for heating, and another as a signal/probe, and a separate embodiment of the present invention, is to mix a wavelength-specific dye into the sol gel solution before deposition on the $SiO_2$ or $Al_2O_3$ substrate. This dye will absorb the heating wavelength, while permitting the passage of the probing wavelength(s).

Figure 9:
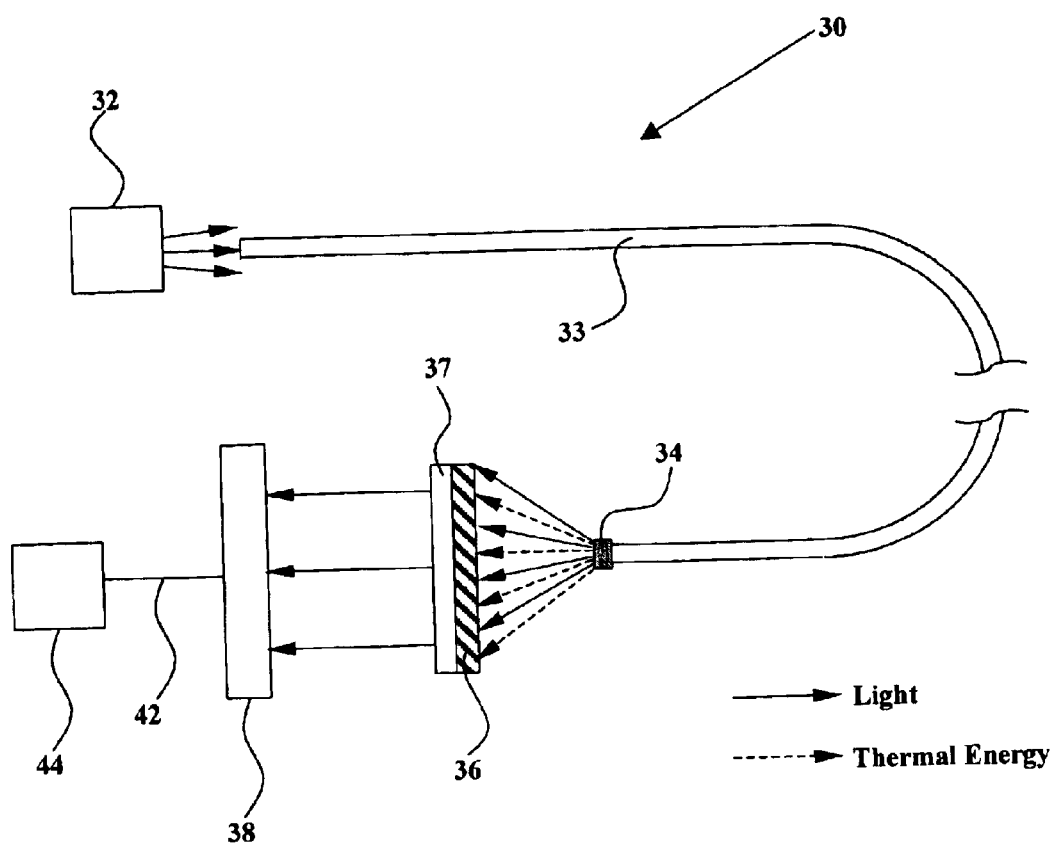
FIG. 9 is a schematic representation of a hydrogen gas detector according to one embodiment in the absence of hydrogen gas, comprising a light/heat source with an optical waveguide having a layered substrate on an optical output surface thereof.

FIG. 9 specifically depicts a hydrogen gas detector 30 comprising a light/heat source 31 with an optical waveguide 33. A polychromatic light source 32 emits light at various wavelength ranges, and the optical waveguide receives and transmits such polychromatic light to a location that is distant from the polychromatic light source 32. A layered substrate 34 is coated on an optical output surface of the optical waveguide 33, for absorbing light at one wavelength to generate thermal energy, while transmitting light at another wavelength. An optical filter comprising a rare earth metal thin film 36 overlaid by a protective layer 37 is arranged in proximity to the layered substrate 34 and the optical output surface of the optical waveguide 33, so that such optical filter is simultaneously illuminated and heated by the light and thermal energy emitted from the layered substrate 34 of the optical waveguide 33. Alternatively, the optical filter may be directly formed on the layered substrate 34 for more efficient light/heat transmission. The heated optical filter of the present invention responses to the presence of hydrogen and recovers in the absence of hydrogen much more rapidly than the unheated optical filter. The light transmitted through the optical filter is detected by a light detector 38, which is joined by output signal transmission wire 42 to output module 44, which may provide a visual, audible, tactile, or other alarm indicative of the presence of hydrogen in the gaseous environment being monitored by the hydrogen gas detector 30. It is important to recognize that the spatial arrangements between the polychromatic light source 32, the optical waveguide 33, the layered substrate 34, and the optical filter are depicted only in an exemplary and illustrative manner in FIG. 9, and are not intended to (therefore should not be construed to) limit the broad scope of the present invention.

The hydrogen gas detectors of the present invention are small, inexpensive, require low power, and are easily maintained. A filly functional detector unit requires only a coated incandescent bulb as described above, a photo-detector, an appropriate power source (that may comprise batteries, making the entire unit self-contained and portable), and a housing that shuts out ambient light but allows for the flow of gas over and around the coated bulb.

In inherently dark environments, such as the interior of pipes, ducts, and similar gas-flow passageways, or interior to normally sealed equipment, no ambient light-blocking housing is necessary.

Alternatively, an ambient light-blocking housing may be avoided by matching the wavelength of light emanating from the optical source with a narrow-band optical detector, the operative wavelength being selected as one not normally included within the ambient lighting conditions at a given location. This may be necessary in certain applications where the coated bulb of the detector must be introduced directly into a gaseous stream, or where the gaseous flow is of such low volume that an ambient light-blocking housing will degrade detection performance.

Multiple optical hydrogen gas detector units may be combined to monitor the presence of hydrogen gas over a large area. Individual unit's detector outputs may all be transmitted, via wired, radio, or optical communications media, to a central processing unit for comprehensive monitoring of an extended area, whereby the output of each sensor is mapped to its individual locus. Such a system could monitor the spread of hydrogen gas throughout an area over time, or calculate safe pathways of egress, selectively activating emergency exit indicia and/or denying access to the areas in which hydrogen is detected.

Alternatively, the output of each individual optical hydrogen gas detector could be connected (i.e., via a relay or transistor) in series arrangement with all other detectors. In this configuration, hydrogen gas detected by any one detector anywhere within the monitored area would result in triggering of, e.g., an alarm or shut-down signal.

Various portable embodiments of the hydrogen gas detector units of the present invention are readily fabricated and utilized. Such portable units may as indicated hereinearlier be battery-powered, as regards the coated bulb, photo-detector, and output module (comprising an output component such as an LED or piezoelectric audible alarm). The portability of such hydrogen gas detector units is a critical safety feature for personnel who must work in environments where hydrogen gas is stored, moved, or utilized.

Portable hydrogen gas detectors according to this embodiment of the present invention could be incorporated into other equipment, with the potential added efficiencies of sharing a power supply or other resources. Examples include lighted hard hats, radio communication devices, battery-powered hand tools, portable computing devices, electronic badges and "smart cards" used for identification and security, etc.

The invention will be further understood and illustrated by the following non-limiting example.

EXAMPLE

A series of hydrogen detectors of the generally type schematically depicted in FIGS. 1 and 2 was fabricated utilizing as the thermally emissive light source in each detector a miniature incandescent lamp (Model #8-374) commercially available from Chicago Miniature Lamp, Inc, (Hackensack, N.J.). These lamp elements have focusing lens-tips, and are rated at 2.5 volts and 0.350 amps. The lamp elements were held with their tips held pointing down in a sample holder and placed in an e-beam evaporator. A first layer of 100 nanometers of gadolinium magnesium alloy was deposited, followed by a layer of 15 nm of palladium. The gadolinium magnesium alloy was created by alternately depositing of gadolinium and then magnesium layers. Two layers of magnesium (15 nm) were layered between 3 layers of gadolinium (23.3 nm), such that the sequence was Gd/Mg/Gd/Mg/Gd, and the total composition ratio was Gd:Mg 70:30 by volume. The deposition was carried out at 300° C., which results in the mixing of the Gd/Mg layers to form an alloy. The bulb was placed in a hydrogen gas test-cell, with appropriate electrical feed-throughs, and powered with a DC power supply. The light output was measured over the spectral range of 650–1100 nm with a fiber optic spectrometer.

Figure 6:
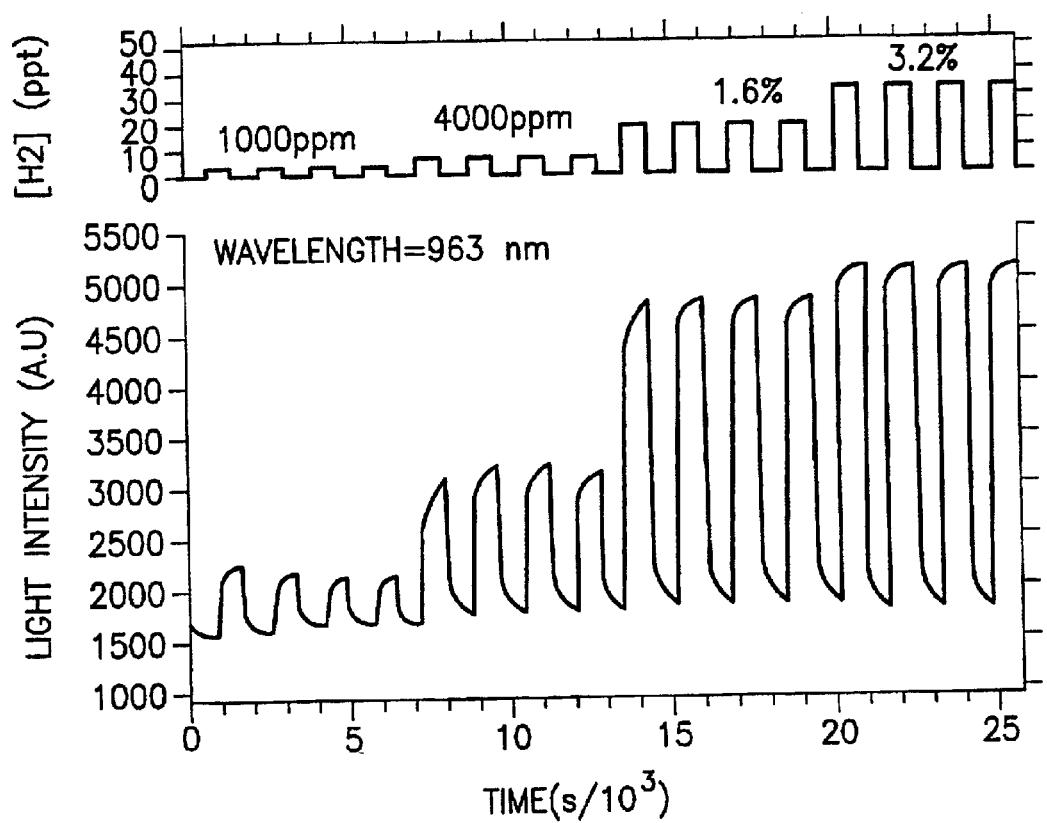
FIG. 6 is a graph depicting a typical optical response curve for the light transmitted through the end of the coated lamp elements in the presence of hydrogen, according to one embodiment of the present invention.

FIG. 6 shows a typical optical response curve for the light transmitted through the end of the coated lamp elements in the presence of hydrogen. In this experiment, the background gas flow was 1000 sccm of air at atmospheric pressure. The concentrations of hydrogen tested were 1000 ppm, 4000 ppm, 1.6% and 3.2%, and each concentration was cycled on and off four times. The lamp element was powered at less than full rating, with 2 volts, and ~0.3 amps. The wavelength of light shown in the graph of FIG. 6 is 963 nm. In general, the response was similar for other wavelengths in the range measured.

Figure 7:
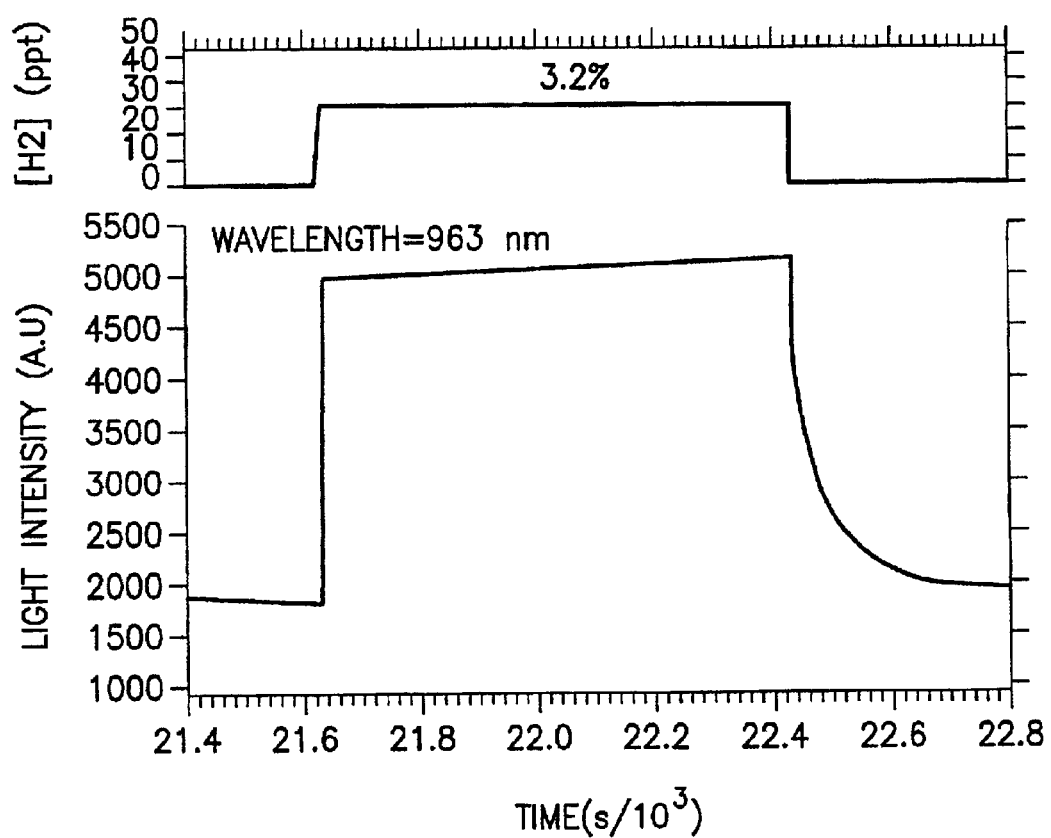
FIG. 7 is a graph depicting the time response curves of hydrogen detectors according to one embodiment of the present invention, in differing concentrations of hydrogen.
Figure 8:
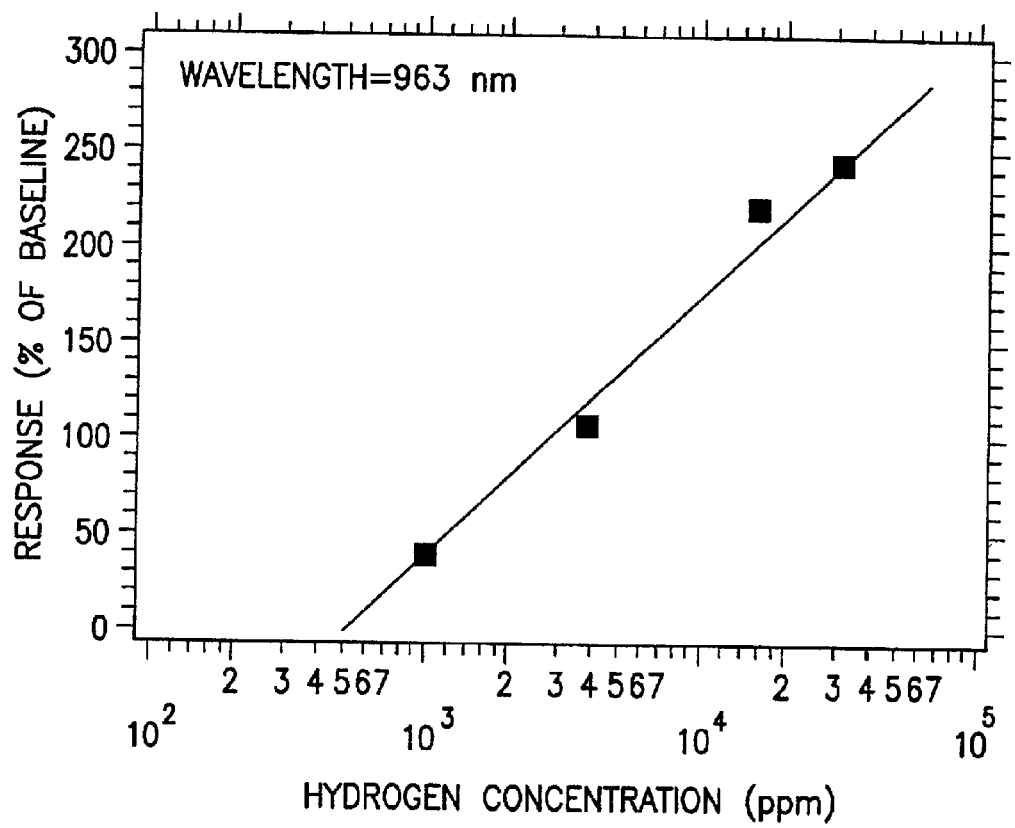
FIG. 8 is a graph depicting the maximum response of one embodiment of the present invention as a function of hydrogen concentration.

FIG. 7 shows an expanded region of the data from FIG. 6 for the purpose emphasizing the speed of response. At 3.2% hydrogen exposure, the response (increasing transmission) reaches 78% of its maximum in 12 s, while the recovery (decreasing transmission) takes 85 s to reach 78% of its return to baseline. These times are significantly faster than the response and recovery times of unheated films, which are on the order of 720 and 2400 s, respectively. It is also expected that these times could be further improved by empirical experimentation and optimization of the thin film processing by someone skilled in the art.

FIG. 6 also shows that concentrations of 1000 ppm were easily detected, and that the response increases with increasing hydrogen concentration. This increase is plotted in FIG.

8, which shows the response as a percent of the baseline as a function of hydrogen concentration. This is particularly useful, as some sensor applications require output signals at different concentrations of hydrogen, e.g., a sensing of 1% hydrogen might trigger a warning light, and a sensing of 2% hydrogen might trigger a relay that shuts a system off. Extrapolation of the data suggests a lower detectable limit of 500 ppm. Also particularly advantageous, is the magnitude of the response, which is greater than 200% at 3.2% hydrogen concentration, and provides a substantial signal to noise ratio. This is useful in minimizing false alarms in a sensor device.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A hydrogen gas detector for detection of hydrogen gas an a gaseous environment, said detector comprising a light/heat source that comprises an incandescent lamp with a light-transmissive bulb and generates both light and thermal energy, an optical detector, and an optical barrier thin film coated over an exterior surface of said light-transmissive bulb of the incandescent lamp, wherein the optical barrier thin film is simultaneously illuminated and heated by said incandescent lamp to an elevated temperature, wherein the heated optical barrier thin film responds to the presence of hydrogen by responsively changing from a first optical state to a different second optical state, and wherein transmission of light from said light/heat source through said heated optical barrier thin film is altered by the presence of hydrogen and said altered transmission is sensed by said optical detector to provide an indication of the presence of hydrogen gas in the gaseous environment.

2. The hydrogen gas detector of claim 1, wherein the first optical state comprises a state of optical opacity of the heated optical barrier thin film.

3. The hydrogen gas detector of claim 1, wherein the second optical state comprises a state of optical non-opacity of the heated optical barrier thin film.

4. The hydrogen gas detector of claim 1, wherein the second optical state comprises translucency/transparency of the heated optical barrier thin film.

5. The hydrogen gas detector of claim 1, wherein the optical barrier thin film comprises a rare earth metal thin film.

6. The hydrogen gas detector of claim 1, wherein the optical barrier thin film comprises an yttrium thin film.

7. The hydrogen gas detector of claim 1, wherein the optical barrier thin film comprises a rare earth metal thin film overlaid by a protective film that is permeable to hydrogen gas.

8. The hydrogen gas detector of claim 7, wherein the protective film comprises a palladium film.

9. The hydrogen gas detector of claim 1, embodied in a unitary portable article.

10. The hydrogen gas detector of claim 1, further comprising a power supply.

11. The hydrogen gas detector of claim 10, wherein the power supply comprises a battery.

12. The hydrogen gas detector of claim 1, further comprising an output module operatively coupled to the optical detector, and arranged to provide an output alarm indicative of the presence or concentration of hydrogen gas in the gaseous environment.

13. The hydrogen gas detector of claim 12, wherein said output alarm is selected from the group consisting of visual, audible and tactile alarms.

14. The hydrogen gas detector of claim 1, of a hand-held size and portable character.

15. The hydrogen gas detector of claim 1, wherein a plurality of light/heat sources, optical detectors, and optical barrier thin films, each set of which is arranged in operative relationship to effect the detection of hydrogen gas in a gaseous environment, are further arranged in an array, and wherein each combination of light/heat source, optical detector, and optical barrier thin film is configured to respond to a different concentration of hydrogen gas in the gaseous environment.

16. The hydrogen gas detector array of claim 15, further comprising a corresponding array of output modules operatively coupled to the optical detectors, and arranged to provide an output indicative of the concentration of hydrogen gas in the gaseous environment.

17. The hydrogen gas detector of claim 1, operatively coupled with corresponding hydrogen gas detectors to form an extended area monitoring system for detection of hydrogen gas in the gaseous environment of said extended area.

18. The hydrogen gas detector of claim 1, wherein the the optical barrier thin film comprises an yttrium thin film with a palladium film coated thereon.

19. A hydrogen gas detector for detection of hydrogen gas in a gaseous environment, said detector comprising a light/heat source that generates both light and thermal energy, an optical detector, and an optical barrier therebetween, wherein the light/heat source is constructed and arranged for simultaneously illuminating the optical barrier and heating same to an elevated temperature, wherein the heated optical barrier responds to the presence of hydrogen by responsively changing from a first optical state to a different second optical state, and wherein transmission of light from light/heat source through said heated optical barrier is altered by the presence of hydrogen and said altered transmission is sensed by said optical detector to provide an indication of the presence of hydrogen gas in the gaseous environment, wherein the optical barrier comprises a rare earth metal thin film deposited on an optical output surface of the light/heat source, wherein surface morphology roughness of the optical output surface of the light/heat source prior to deposition of the rare earth metal thin film has been increased by treatment of the optical output surface comprising a roughening step selected from the group consisting of mechanical roughening, chemical roughening, deposition of highly exfoliated or porous inorganic underlayers, and deposition of porous polymer underlayers, to thereby increase the response time of the rare earth metal thin film as compared with a corresponding unroughened optical surface.

20. A hydrogen gas detector for detection of hydrogen gas in a gaseous environment, said detector comprising a light/heat source that comprises an optical waveguide that provides light at a first and a second wavelength, an optical detector, and an optical barrier therebetween, wherein optical output surface of said optical waveguide comprises a layered substrate that absorbs light at said first wavelength to generate thermal energy for heating the optical barrier to an elevated temperature and simultaneosly transmits light at said second wavelength for illuminating said optical barrier, wherein the heated optical barrier responds to the presence of hydrogen by responsively changing from a first optical state to a different second optical state, and wherein transmission of light from said light/heat source through said heated optical barrier is altered by the presence of hydrogen and said altered transmission is sensed by said optical detector to provide an indication of the presence of hydrogen gas in the gaseous environment, wherein the optical barrier comprises a rare earth metal thin film deposited on an optical output surface of the light/heat source.

21. The hydrogen gas detector of claim 20, wherein optical output surface of said optical waveguide is coated with a rare earth metal thin film as said optical barrier.

22. A hydrogen gas detector for detection of hydrogen gas in a gaseous environment, said detector comprising at least one light/heat source that comprises an incandescent lamp with a light-transmissive bulb and generates both light and thermal energy, at least one optical detector, and at least one optical barrier thin film coated over an exterior surface of said light-transmissive bulb of the incadescent lamp, wherein the at least one optical barrier thin film simultaneously illuminated and heated by said at least one light/heat source to an elevated temperature, wherein the heated optical barrier thin film responds to the presence of hydrogen by responsively changing from a first optical state to a different second optical state, whereby transmission of light from said light/heat source through said heated optical barrier thin film is altered by the presence of hydrogen and said altered transmission is sensed by said at least one optical detector to provide an indication of the presence and concentration of hydrogen gas in the gaseous environment.

23. The hydrogen gas detector of claim 22, wherein the at least one optical barrier thin film comprises a single rare earth metal thin film with a plurality of protective layer sections overlaid on mutually exclusive portions of the rare earth metal thin film, wherein each protective layer section exhibits a unique permeability to hydrogen.

24. The hydrogen gas detector of claim 23, wherein the number of optical detectors exceeds the number of light/heat sources, and wherein each optical detector is arranged in light-receiving relationship with a light/heat source such that the luminous flux impinging each detector passes through only one of the plurality of protective layer sections.

25. A hydrogen gas detector of claim 24, further comprising a plurality of output modules, each of which is operatively coupled to an optical detector, and arranged to provide an output indicative of the concentration of hydrogen gas in the gaseous environment.

26. A method of fabricating a hydrogen gas detector, comprising:
    providing an incandescent lamp with a light-transmissive bulb having an output surface for emitting light and thermal energy;
    depositing on the output surface of said light-transmissive bulb an optical filter layer comprising a rare earth metal thin film that responds to contact with hydrogen by exhibiting a detactable change of optical transmissivity;
    positioning a light detector in light-sensing proximity to the incandescent lamp, whereby a change in optical transmissively of the rare earth metal thin film in exposure to hydrogen gas is detected as a change in luminous energy flux impinging on the detector, and
    outputting a signal indicative of said change in luminous energy flux.

27. The method according to claim 26, wherein the rare earth metal thin film is formed on the output surface of the light-transmissive bulb of the incandescent lamp, by a technique selected from the group consisting of physical vapor deposition, chemical vapor deposition, sputtering, solution deposition, focused ion beam deposition, pulsed laser deposition, electrolytic plating, and electroless plating.

28. The method according to claim 26, wherein the rare earth metal thin film is formed by physical vapor deposition.

29. The method according to claim 26, wherein the rare earth metal thin film is formed by chemical vapor deposition using an organometallic precursor that thermally decomposes to the metal hydride or elemented metal in a reducing environment of hydrogen.

30. The method according to claim 26, wherein the outputting step comprises generating an output selected from the group consisting of visual outputs, optical outputs, tactile outputs, electrical outputs and auditory outputs.

31. The method according to claim 26, wherein the rare earth metal thin film comprises at least one metal selected from the group consisting of:
    (I) scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, and lawrencecium,
    (II) alloys thereof, and
    (III) alloys containing one or more of such metals alloyed with an alloying component selected from the group consisting of magnesium, calcium, barium, strotium, cobalt and iridium.

32. The method according to claim 26, wherein the rare earth metal thin film comprises a rare earth metal component selected from the group consisting of trivalent rare earth metals reactive with hydrogen to form both metal dihydride and metal trihydride reaction products, and wherein the metal dihydride and metal trihydride reaction products have differing optical transmissivity, and wherein transitions between the metal dihydride and metal trihydride reaction products are caused by the presence or absence of hydrogen gas contacting the rare earth metal thin film.

33. The method according to claim 26, wherein the rare earth metal thin film is overlaid by a hydrogen-permeable material comprising a metal selected from the group consisting of Pd, Pt, Ir, Ag, Au, Ni, Go, and alloys thereof.

34. The method according to claim 26, wherein the rare earth metal film is overlaid by hydrogen-permeable material that is doped with a dopant selected from the group consisting of Mg, Ca, Al, Ir, Ni and Co.

35. The method according to claim 26, wherein the rare earth metal thin film is overlaid by a thin film of a material including a metal selected from the group consisting of palladium, platinum, and iridium.

36. The method according to claim 26, wherein the rare earth metal thin film comprises yttrium.

37. The method according to claim 26, wherein the rare earth metal thin film comprises a metal selected from the group consisting of lanthanum and yttrium, and the rare earth metal thin film is formed on the output surface of the light-transmissive bulb of the incandescent lamp by CVD utilizing a corresponding precursor, wherein said precursor is selected from the group consisting of tris (cyclopentadienyl) lanthanum, tri(cyclopentadienyl)yttrium, β-diiminate complexes of lanthanum, β-diiminate complexes of yttrium, lantanum amides, and yttrium amides.

38. The method according to claim 26, wherein the rare earth metal thin film comprises lantanium, and the rare earth metal thin film is formed on the substrate by CVD utilizing a precursor, wherein said precursor is selected from the group consisting of La(NR$_2$)$_3$, La(NR$_2$)$_3$ L, La(R)$_3$ and La(R)$_3$ L, wherein R is selected from the group consisting of C$_1$ to C$_8$ alkyl and C$_1$ to C$_1$ to C$_8$ aryl L is a Lewis base ligand selected from the group consisting of amines, aryls, and aryl amines.

39. The method according to claim 38, wherein the Lewis base ligand is selected from the group consisting of NH3, primary amines, secondary amines, tertiary amines, polyamines.

40. The method according to claim 39, wherein the Lewis base ligand is selected from the group consisting of pyridine, methylamine, dimethylamine trimthylamine, dimethylethlamine, *N,N,N', N'*-tetramethylethylenediamine and *N,N,N',N',N'-pentamethyldiethylenetriamine*.

41. The method according to claim 26, wherein the rare earth metal thin film comprises yttrium, and the rare earth metal thin film is formed by CVD utilizing a precursor, wherein said precursor is Y(NSI'3)3, wherein R$^1$ is selected from the group consisting of C$_1$ to C$_8$ alkyl and C$_1$ to C$_8$ aryl.

42. The method according to claim 26, wherein the rare earth metal thin film has deposited thereon with an overlayer comprising palladium, and said overlayer is formed by chemical vapor deposition on the rare earth metal thin film using a palladium precursor selected from the group consisting of Pd(hfac)$_2$, Pd(allyl)$_2$, CpPd(allyl), Pd(allyl)(hfac), COD-Pd(Me)$_2$ and Pd(methylallyl)(hfac).

\* \* \* \* \*

UNITED STATES PATENT AND TRADEMARK OFFICE
CERTIFICATE OF CORRECTION

PATENT NO. : 6,897,960 B2  
DATED : May 24, 2005  
INVENTOR(S) : Frank Dimeo, Jr. et al.

Page 1 of 1

It is certified that error appears in the above-identified patent and that said Letters Patent is hereby corrected as shown below:

Column 9,  
Line 19, "La(R)$_3$.L" should be -- La(R)$_3$·L --.  
Line 39, "COD.Pd(Me)$_2$" should be -- COD·Pd(Me)$_2$ --.  
Line 50, "Go" should be -- Co --.

Column 10,  
Line 17, "10'" should be -- 10 --.

Column 17,  
Line 23, "an" should be -- in --.

Column 20,  
Line 24, "lawrencecium" should be -- lawrencium --.

Column 21,  
Line 1, "La(NR$_2$)$_3$ L" should be -- La(NR$_2$)$_3$ ·L --.  
Line 3, "C$_1$ to C$_1$ to C$_8$ aryl L" should be -- C$_1$ to C$_8$ aryl and L --.  
Line 14, "N, N, N', N', N''" should be -- N, N, N', N', N" --.

Column 22,  
Line 4, "Y(NSI'3)3" should be -- Y(NSiR'$_3$)$_3$ --.  
Line 4, "R$^1$" should be -- R' --.  
Line 12, "COD-Pd(Me)$_2$" should be -- COD·Pd(Me)$_2$ --.

Signed and Sealed this

Eleventh Day of October, 2005

JON W. DUDAS  
*Director of the United States Patent and Trademark Office*